(12) United States Patent
Hematti et al.

(10) Patent No.: US 8,647,678 B2
(45) Date of Patent: Feb. 11, 2014

(54) ANTI-INFLAMMATORY MACROPHAGES AND USES THEREOF

(75) Inventors: Peiman Hematti, Madison, WI (US); Jaehyup Kim, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 171 days.

(21) Appl. No.: 12/862,506

(22) Filed: Aug. 24, 2010

(65) Prior Publication Data

US 2011/0045071 A1 Feb. 24, 2011

Related U.S. Application Data

(60) Provisional application No. 61/236,427, filed on Aug. 24, 2009.

(51) Int. Cl.
*A61K 35/28* (2006.01)
*C12N 5/08* (2006.01)

(52) U.S. Cl.
USPC .......................................... 424/577; 435/372

(58) Field of Classification Search
None
See application file for complete search history.

(56) References Cited

U.S. PATENT DOCUMENTS

2006/0210543 A1 9/2006 Leor et al.

FOREIGN PATENT DOCUMENTS

WO 95/09639 A1 4/1995

OTHER PUBLICATIONS

Yang et al Zhonghua Xue Ye Xue Za Zhi, 2008, 29(8) ,Abstrac,t.*
Yang et al (Zhonghua Xue Ye Xue Za Zhi, 2008, 29(8)).*
Ivanova-Todorova E. et al., "Adipose tissue-derived mesenchymal stem cells are more potent suppressors of dendritic cells differentiation compared to bone marrow-derived mesenchymal stem cells," Immunology Letters, Elsevier VB, NL, Jul. 30, 2009, vol. 126, No. 1-2, pp. 37-42.
Jiang Xiao-Xia et al., "Human mesenchymal stem cells inhibit differentiation and function of monocyte-derived dendritic cells," Blood, May 2005, vol. 105, No. 10, pp. 4120-4126.
Kim J. et al., "Mesenchymal stem cell-educated macrophages: A novel type of alternatively activated macrophages," Experimental Hematology, Elsevier Inc., US, Dec. 1, 2009, vol. 37, No. 12, pp. 1445-1453.
Martinez, F.O. et al., "Transcriptional profiling of the human monocyte-to -macrophage differentiation and polarization: New Molecules and patterns of gene expression", 2006, J. Immunol., vol. 177, pp. 7303-7311.
Xu, W. et al., "Human peritoneal macrophages show functional characteristics of M- CSF- driven anti-inflammatory type 2 macrophages", 2007, Eur. J. Immunol., vol. 37, 1594-1599.

* cited by examiner

*Primary Examiner* — Michail Belyavskyi
(74) *Attorney, Agent, or Firm* — Quarles & Brady LLP (57) ABSTRACT

The invention relates to a purified, novel anti-inflammatory population of macrophage and methods of making and using such macrophage.

9 Claims, 6 Drawing Sheets

ANTI-INFLAMMATORY MACROPHAGES AND USES THEREOF

CROSS-REFERENCE TO RELATED APPLICATION

This application claims the benefit of U.S. Provisional Patent Application No. 61/236,427, filed Aug. 24, 2009, incorporated herein by reference as if set forth in its entirety.

STATEMENT REGARDING FEDERALLY SPONSORED RESEARCH OR DEVELOPMENT

This invention was made with United States government support awarded by the following agencies: NIH HL 081076. The United States government has certain rights in this invention.

BACKGROUND

Mesenchymal stem cells (MSCs) are fibroblast-like cells that reside within virtually all tissues of a postnatal individual. Within bone marrow (BM), from which they were first isolated more than 40 years ago, MSCs provide the stromal support tissue for hematopoietic stem cells. In addition, MSCs can differentiate into cells of the mesenchymal lineage, such as osteoblasts, adipocytes, and chondrocytes. MSCs can interact with immune cells at various activation stages in vitro and modulate the immune cells' activity through a variety of mechanisms. Tse et al., Transplantation 75:389-397 (2003); Le Blanc et al., Exp. Hematol. 31:890-896 (2003); Rasmusson et al., Transplantation 76:1208-1213 (2003); Di Ianni et al., Exp. Hematol. 36:309-318 (2008).

Because of their regenerative and immunomodulatory properties, MSCs are implicated in the treatment of a great number of disorders associated with aberrant immune function and inflammation. Le Blanc et al., Cytotherapy. 7:36-45 (2005); Jones et al., Exp. Hematol. 36:733-741 (2008); Javazon et al., Exp. Hematol. 32:414-425 (2004). Ongoing phase I-III clinical trials examine the use of MSCs as possible treatment of a variety of disorders. For example, MSCs made from allogeneic third party BM are effective in treating acute graft versus host disease after allogeneic hematopoietic stem cell transplantation. Le Blanc et al., Lancet. 371:1579-1586 (2008). Also, allogeneic or autologous MSCs from BM or other tissues are being examined as treatment for a wide variety of conditions, such as myocardial infarction, amyotrophic lateral sclerosis, stroke, Crohn's disease, diabetes mellitus, and refractory non-healing wounds. Yoshikawa et al., Plast. Reconstr. Surg., 121:860-877 (2008). A major obstacle to using BM-derived MSCs in a clinical setting is the time, usually several weeks, needed to culture and expand a sufficient number of MSCs for application.

While the interaction of MSCs with T-lymphocytes, B-lymphocytes, natural killer cells, and dendritic cells have been extensively studied, little is known about the interaction of MSCs with other cells of the monocytic lineage, specifically macrophages. Macrophages are widely distributed in many different tissues and are a key component of innate immunity. Like other hematopoietic cells, macrophages originate from a bone marrow precursor cell that first gives rise to monocytes. Monocytes circulate in the peripheral blood and can give rise to macrophages after extravasating from the blood stream into the surrounding tissue, either to replace long-lived tissue macrophages or in response to injury. Gordon, European J Immunol. 37 Suppl 1:S9-17 (2007).

Studies with murine macrophages and MSCs demonstrated that MSC-conditioned media inhibits the capacity of an activated murine leukemic monocyte/macrophage cell line (RAW-264.7) to secrete TNF-α. Ortiz et al., PNAS 104:11002-11007 (2007). Further, LPS-stimulated macrophages produced more IL-10 when co-cultured with murine MSCs. Significantly more of the macrophages isolated from septic mice treated with MSCs contained intracellular IL-10. Nemeth et al., Nature Med. 15:42-49 (2009). However, these studies were conducted using murine cells, which differ in many regards from human MSCs or macrophages. Peister et al., Blood 103:1662-1668 (2004); Schneemann and Schoeden, J Leukocyte Biol. 81:579 (2007), each of which is incorporated herein by reference as if set forth in its entirety. The inventors were first to study human macrophage-MSC interactions.

Although various categories of classification have been proposed, macrophages are typically divided into classically-activated macrophages (M1 macrophages) and alternatively-activated macrophages (M2 macrophages). Martinez et al., Annu. Rev. Immunol. 27:451-483 (2009). Generally, M1 macrophages exhibit potent anti-microbial properties, reminiscent of type 1 T-helper lymphocyte (Th1) responses. In contrast, M2 macrophages promote type 2 T-helper lymphocyte (Th2)-like responses, secrete less pro-inflammatory cytokines, and assist resolution of inflammation by trophic factor synthesis and phagocytosis. Mosser et al., Nature Rev. 8:958-969 (2008). M2 macrophages can be further divided into three distinct subclasses, i.e., M2a, M2b, and M2c, defined by specific cytokine profiles. Mantovani et al., Trends Immunol. 25:677-686 (2004). While M2 macrophages are generally characterized by low production of pro-inflammatory cytokines, such as IL-12, and high production of anti-inflammatory cytokines such as IL-10, M2b macrophages retain high levels of inflammatory cytokine production, such as TNF-α and IL-6. Mosser, J. Leukocyte Biol. 73:209-212 (2003).

Macrophages can be polarized by their microenvironment to assume different phenotypes associated with different stages of inflammation and healing. Stout et al., J. Immunol. 175:342-349 (2005). Certain macrophages are indispensible for wound healing. They participate in the early stages of cell recruitment and of tissue defense, as well as the later stages of tissue homeostasis and repair. Pollard, Nature Rev. 9:259-270 (2009). Macrophages derived from peripheral blood monocytes have been used to treat refractory ulcers. Danon et al., Exp. Gerontol. 32:633-641 (1997); Zuloff-Shani et al., Transfus. Apher. Sci. 30:163-167 (2004), each of which is incorporated herein by reference as if set forth in its entirety.

BRIEF SUMMARY

The present invention is broadly summarized as relating to a new subset of anti-inflammatory macrophages. These macrophages can be generated by co-culturing CD14$^+$ cells with MSCs and can be used to treat disorders associated with aberrant inflammation. While macrophages have previously been used to treat refractory ulcers, the inventors generated a novel type of anti-inflammatory macrophage, through MSC co-culture, that acts as an effector cell of MSCs.

In a first aspect, the invention relates to a novel type of anti-inflammatory macrophage characterized by high levels of IL-10 and IL-6 expression and low levels of IL-12 and TNF-α expression.

In a second aspect, the invention is summarized in that a method for producing a novel anti-inflammatory macrophage includes the step of co-culturing a CD14$^+$ cell and an MSC in vitro to produce a macrophage characterized by high levels of IL-10 and IL-6 expression and low levels of IL-12 and TNF-α expression.

In a third aspect, the invention relates to methods for treating disorders associated with aberrant inflammation comprising the step of administering to an individual anti-inflammatory macrophages characterized by high levels of IL-10 and IL-6 expression and low levels of IL-12 and TNF-α expression.

In a fourth aspect, the invention relates to compositions comprising MSC-educated macrophages effective to alleviate conditions associated with inflammation.

Unless otherwise defined, all technical and scientific terms used herein have the same meaning as commonly understood by one of ordinary skill in the art to which this invention belongs. Although suitable materials and methods for the practice or testing of the present invention are described below, other materials and methods similar or equivalent to those described herein, which are well known in the art, can be used.

Other objectives, advantages and features of the present invention will become apparent from the following specification taken in conjunction with the accompanying drawings.

DETAILED DESCRIPTION OF PREFERRED EMBODIMENTS

The present invention broadly relates to a novel type of anti-inflammatory macrophage characterized by high levels of IL-10 and IL-6 expression and low levels of IL-12 and TNF-α expression as well as methods for making and using such macrophage. The novel anti-inflammatory macrophage is useful for modulating the inflammatory response when administered to an individual. As used herein, "macrophage" refers to a mononuclear phagocyte characterized by the expression of CD 14 and lack of expression of dendritic cell markers.

As used herein, "monocyte" refers to a mononuclear leukocyte that can differentiate into a macrophage.

$CD14^+$ cells are co-cultured in vitro with MSCs to yield MSC-educated macrophages characterized by an IL-10 high, IL-6 high, IL-12 low, and TNF-α low immunophenotype. As used herein, "$CD14^+$ cell" refers to a monocyte or a macrophage.

$CD14^+$ cells and MSCs used for co-culture can be derived from any suitable source. The skilled artisan will appreciate the advantageous efficiency of generating macrophages from peripheral blood monocytes for MSC co-cultures. Alternatively, macrophages can also be isolated from an individual directly, such as through cellular outgrowth from tissue samples. Monocytes isolated from peripheral blood can be cultured for various times and under various conditions before MSCs co-culture or can be added to MSCs directly for co-culture. Suitable sources for MSCs include, but are not limited to, bone marrow, placental-derived stem cells, adipose stem cells, embryonic stem cells, and induced pluripotent stem cells.

The skilled artisan will appreciate that monocytes, macrophages, and MSCs employed in methods described herein can be cultured in any medium that supports their survival and growth. Co-cultures do not require the addition of cytokines. MSCs and macrophages can be autologous, syngeneic, or allogeneic with respect to each other.

For MSC-macrophage co-culture, monocytes or macrophages can be co-cultured with MSCs such that the cells are in direct physical contact. Alternatively, the cells can be placed in subcompartments that are in fluid communication but separated by a semi-permeable membrane. The semi-permeable membrane allows the exchange of soluble media components and factors secreted by the cells but is impenetrable for the cells themselves. The pores within the semi-permeable membrane typically are between 0.1-1.0 µm, but other pore sizes can be suitable.

As used herein, "MSC-educated macrophage" refers to an anti-inflammatory macrophage that was generated by co-culturing a $CD14^+$ cell with an MSC. MSC-educated anti-inflammatory macrophages described herein are readily distinguished from existing macrophages in that they express a unique cytokine profile. Like M2b macrophages, MSC-educated macrophages express high levels of IL-10 and low levels of IL-12. Unlike M2b macrophages, MSC-educated macrophages also express high levels of IL-6 and low levels of or no TNF-α. Thus, the immunophenotype characterized of this novel MSC-educated macrophage population can be summarized as IL-10 high, IL-6 high, IL-12 low, and TNF-α low cytokine expression.

As used herein, "high" means that the cells are characterized by higher expression of a particular cytokine compared to control macrophages cultured without MSCs. For example, "IL-6 high" indicates that macrophages co-cultured with MSCs express higher amounts of IL-6 than macrophages that have not been co-cultured with MSCs. Similarly, "low" means that the cells are characterized by lower expression of a particular cytokine, e.g., IL-12 low indicates lower expression of IL-12. "Low" can also mean that the expression levels are below the detection limit.

Various methods of cell separation and isolation are known in the art and can be used to separate the MSC-educated macrophages from the MSCs depending on factors such as the desired purity of the isolated cell populations. For example, MSC-educated macrophages can be isolated using flow cytometry based on intracellular cytokine expression. MSC-educated anti-inflammatory macrophages can be maintained in culture in any medium that supports macrophages in vitro. Also, MSC-educated macrophages can be stored using methods known in the art including, but not limited to, refrigeration, cryopreservation, vitrification, and immortalization.

It is contemplated that MSC-educated macrophages can be administered to an individual for treating conditions associated with aberrant inflammation and immune function. Conditions associated with aberrant inflammation include, but are not limited to, organ transplantation, graft versus host disease, myocardial infarction, non-healing wounds, and diabetes. Specifically contemplated herein is a method for accelerating wound healing in an individual in need thereof, comprising administering MSC-educated macrophages to the individual.

It is specifically contemplated that one can provide sufficient autologous MSC-educated macrophages for clinical application by co-culturing autologous monocytes or macrophages with allogeneic MSCs from a universal source. MSC-educated macrophages administered to an individual can be autologous, syngeneic, or allogeneic. References herein to an "autologous" macrophage indicate that the MSC-educated macrophage is returned to the same individual from which the monocyte or macrophage was taken and used to generate the anti-inflammatory macrophage.

One application for IL-10 high, IL-6 high, IL-12 low, and TNF-α low MSC-educated macrophages contemplated by the inventors is to promote healing of chronic wounds. IL-10 increases healing and reduce scar formation. While IL-6, along with other pro-inflammatory cytokines, can be associated with inflammatory conditions, endogenous IL-6 from tissue macrophages can also be anti-inflammatory in both local and systemic inflammatory responses. Xing et al., J. Clin. Invest. 101:311-320 (1998). IL-6 is also important for normal wound repair, as is evident from the delayed wound healing observed in IL-6-deficient mice. Gallucci et al., FASEB J. 14:2525-2531 (2000). IL-6 can also restore normal wound repair in immunosuppressed mice. Gallucci et al., J. Interferon Cytokine Res. 21:603-609 (2001).

The macrophages can be administered to an individual through any suitable delivery method. A delivery method can include topical application to a wound. For example, macrophages can be delivered in a pharmaceutically acceptable carrier or dressing, examples of which include a liquid, oil, lotion, salve, cream, foam, gel, paste, powder, film, or hydrogel. Exemplary carriers and dressings having suitable properties are well-known by those of ordinary skill in the art. The choice of a specific carrier is influenced by factors such as nature of the condition, number of cells to be administered, route of administration, and duration of treatment. Macrophages can also be delivered through local or systemic injection or other methods known in the art. Macrophages can be autologous, syngeneic, or allogeneic with respect to the receiving individual and with respect to MSCs used for their education.

The term "wound," as used herein, broadly includes any injury of or damage to a tissue, including, but not limited to, skin. Such damage can be the result of varying causes, such as trauma, pressure, friction, abrasion, vascular insufficiencies, ischemia, infection, immunological and inflammatory conditions, and exposure to heat, cold, or chemicals. Examples of wounds include, but are not limited to, myocardial infarction, ulcers, and dermal wounds, such as incisions, excisions, scrapes, and burns. The term "chronic wound," as used herein, means a wound that fails to heal within a time frame accepted or acceptable by the skilled artisan.

As used herein, "improved wound healing" means the improvement of at least one wound healing parameter including, but not limited to, accelerated wound closure, decreased wound area, accelerated reepithelialization, increased granulation tissue formation, increased collagen formation, decreased tissue degradation, improved scarring, reduced inflammation, increased tensile strength, increased cell proliferation, and increased angiogenesis.

The invention will be more fully understood upon consideration of the following non-limiting Examples.

EXAMPLES

Example 1

Isolation of Human Monocytes and Mesenchymal Stem Cells

All protocols were approved by the Health Sciences Institutional Review Board of University of Wisconsin-Madison School of Medicine and Public Health.

Monocytes were derived from peripheral blood of human volunteers. Monocytes were isolated from human peripheral blood using magnetic bead separation according to manufacturer's instructions, briefly described as follows. Peripheral blood mononuclear cells were isolated from the blood of healthy volunteers by density gradient separation using Percoll (GE Healthcare Bio-sciences, Piscataway, N.J., USA). Contaminating red blood cells were lysed by incubating the mononuclear cells in ACK lysis buffer for 3 minutes, followed by a wash in phosphate buffered saline (PBS). To reduce platelet contamination, the cells were centrifuged at 700 rpm for 15 minutes. The resulting cell pellets were resuspended and incubated with MicroBeads conjugated to anti-human CD14 antibodies (Miltenyi Biotech, Auburn, Calif., USA) for 15 minutes at 4° C. degree. The cells were washed to remove unbound antibody, and separated using autoMACS Pro Separator (Miltenyi Biotech). Ninety-five percent of the purified cells expressed CD14, as determined by flow cytometry. Purified CD14+ monocytes were plated into the wells of 6-well cell culture plates at a concentration of $0.5$-$1 \times 10^6$ cells per well in IMDM media supplemented with 10% human serum blood type AB (Mediatech, Herndon, Va., USA), 1× non-essential amino acids (NEAA-Lonza, Walkersville, Md., USA), 4 mM L-Glutamine (Invitrogen, Carlsbad, Calif., USA), 1 mM Sodium pyruvate (Mediatech), and 4 µg/ml recombinant human insulin (Invitrogen). To generate macrophages, $CD14^+$ monocytes were cultured at 37° C. with 5% $CO_2$ for approximately 3-7 days, without adding any cytokines, changing the media once 3-4 days after initiating the cultures.

MSCs were isolated from filters left over from standard filtration of bone marrow harvests from healthy donors. Briefly, the bone marrow cells trapped in the filter were collected by washing the filter with PBS. Mononuclear cells were separated using Ficoll-Hypaque 1.073 (GE Healthcare Bio-sciences) and Leucosep tube (Greiner Bio-one, Monroe, N.C., USA) according to the manufacturer's instructions. Contaminating red blood cells were lysed by incubating the mononuclear cells in ACK lysis buffer for 3 minutes. Mononuclear cells were suspended in alpha minimum essential medium (αMEM) supplemented with 10% fetal bovine serum (FBS-Hyclone, Logan, Utah, USA), 1×NEAA, and 4 mM L-Glutamine. Cells that attached to the culture dish (passage 0) were harvested using TrypLE cell dissociation enzyme (Invitrogen) and then replated into new flasks, as described by Trivedi and Hematti, Exp. Hematol. 36:350-359 (2008), incorporated herein by reference as if set forth in its entirety. Passage 4 cells were characterized by flow cytometry and by multi-differentiation assays for MSC characteristics.

Example 2

MSC-Induced Upregulation of CD206 Expression

Macrophages were derived as described in Example 1. MSCs were harvested from healthy BM and passaged as described in Example 1. Passage 4 MSCs were used for co-culture experiments. Cells were harvested with a cell scraper. Cell surface Fc receptors were blocked with Fc Receptor Blocking agent (Miltenyi Biotech) for 15 minutes at 4° C. to prevent non-specific antibody binding. The respective antibodies recognizing surface antigens, listed in Table 1, were added to the cells, alone or in combination, followed by incubation for 30 minutes at 4° C. in the dark.

TABLE 1

Antibodies used for cell surface marker expression analysis.

| Antibody | Label | Source |
| --- | --- | --- |
| anti-CD1a | Fluorescein isothiocyanate | Miltenyi Biotech |
| anti-CD3 | Allophycocyanin | eBioscience, San Diego, CA, USA |
| anti-CD14 | Allophycocyanin | eBioscience |
| anti-CD14 | Fluorescein isothiocyanate | BD Pharmingen |
| anti-CD29 | Phycoerythrin | BD Pharmingen |
| anti-CD31 | Allophycocyanin | eBioscience |
| anti-CD34 | Fluorescein isothiocyanate | BD Pharmingen |
| anti-CD44 | Phycoerythrin | BD Pharmingen |
| anti-CD45 | Phycoerythrin | eBioscience |
| anti-CD54 | Allophycocyanin | RnD systems, Minneapolis, MN, USA |
| anti-CD73 | Phycoerythrin | BD Pharmingen |
| anti-CD90 | PerCP-Cy5.5 | eBioscience |
| anti-CD90 | Allophycocyanin | BD Pharmingen |
| anti-CD105 | Allophycocyanin | eBioscience |
| anti-CD163 | Phycoerythrin | eBioscience |
| anti-CD163 | Phycoerythrin | BD Pharmingen |
| anti-CD206 | Fluorescein isothiocyanate | BD Pharmingen |
| anti-CD206 | Phycoerythrin | BD Pharmingen |
| anti-CD209 | Fluorescein isothiocyanate | Miltenyi Biotech |
| anti-HLA-ABC | Fluorescein isothiocyanate | eBioscience |
| anti-HLA-DR | Fluorescein isothiocyanate | BD Pharmingen |

The cells were washed and fixed with 1% paraformaldehyde in PBS. Cell surface staining was analyzed within 24 hours of antibody stainting using a FACScalibur flow cytometer (Becton Dickinson, Franklin Lakes, N.J., USA).

All MSCs used for co-culture experiments were positive for the MSC markers CD29, CD44, CD73, CD90, CD105, and negative for the hematopoietic markers CD31, CD34, CD45, CD54 prior to their co-culturing. Staining for the dendritic cell markers CD1a and CD209 confirmed the absence of dendritic cells in the monocyte-derived macrophage cultures and MSC-macrophage co-cultures. MSCs were co-cultured with monocyte-derived macrophages from unrelated donors, generated as described in Example 1. At day 3-7, $2 \times 10^5$ MSCs were added to each well of monocyte-derived macrophages and incubated for an additional three to four days. Student's t-test was performed for statistical analysis. A p-value of less than 0.05 was considered statistically significant. Data are presented as mean±SD.

To distinguish macrophages from MSCs during flow cytometric analysis, co-culture cells were gated using CD90 and CD14. Generally, MSCs express high levels of CD90 on their surface and lack CD14 surface expression, while macrophages express high levels of CD14 on their surface and lack CD90 surface expression. FlowJo software version 7.2.5 (Tree Star, Ashland, Oreg., USA) was used to analyze the acquired data.

Figure 1A:
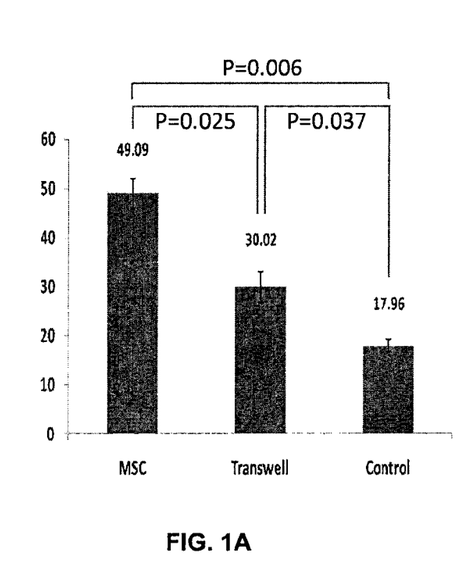
FIG. 1A-B illustrate CD206 cell surface marker expression on macrophages co-cultured in direct contact with MSCs (MSC), macrophages co-cultured with MSCs separated by a semi-permeable membrane insert (Membrane), and macrophages without MSCs (Control).
Figure 1B:
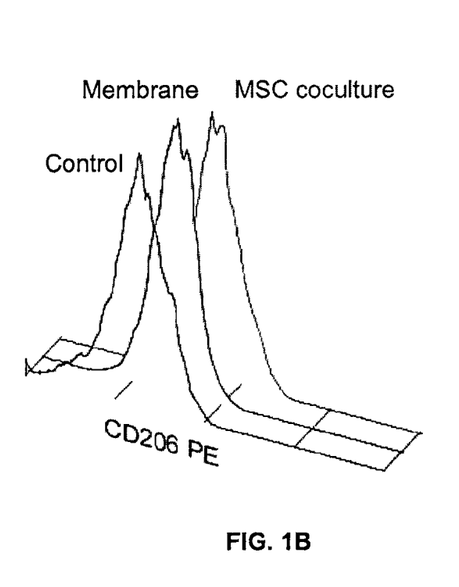

To determine if MSCs alter the immunophenotype of macrophages, cells were stained for CD206, a well-known marker for anti-inflammatory macrophages. Porcheray et al., Clin. Exp. Immunol. 142:481-489 (2005), incorporated herein by reference as if set forth in its entirety. The analysis compared the CD206 mean fluorescence intensity (MFI) of macrophages cultured either alone (control) or co-cultured with MSCs (MSC). The MFI is a numerical value indicative of CD206 expression. Compared to the MFI of CD206 staining on control macrophages, the MFI of CD206 staining was significantly increased on peripheral blood monocyte-derived macrophages co-cultured with MSCs for three to four days (FIG. 1). Control cells had a MFI value of 17.96±1.28, while macrophages co-cultured in direct contact with MSCs had a MFI value of 49.09±3.07. These results suggest that MSCs induce an anti-inflammatory phenotype in macrophages. To determine if direct cell-cell contact is required for the upregulation of CD206 expression, MSCs and macrophages were separated through semi-permeable membrane inserts (TRANSWELL, Corning, Inc.) during co-culture to prevent direct physical contact between MSCs and macrophages. The results from these experiments suggested that physical cell-cell interaction is partly responsible for increased CD206 expression (FIG. 1). Macrophages separated from MSCs by semi-permeable membrane inserts had a MFI value of 30.02±3.11, which is significantly higher than the CD206 expression MFI in control macrophages but significantly lower than CD206 expression MFI of macrophages directly co-cultured with MSCs (FIG. 1, $p<0.05$).

Example 3

MSC-Induced Intracellular Cytokine Expression

MSCs were harvested from healthy BM and passaged as described in Example 1. Macrophages were derived as described in Example 1. MSCs-macrophage co-culture experiments were conducted as described in Example 2. Subsequently, macrophages were examined for intracellular cytokine expression and phagocytosis.

To detect intracellular expression of the various cytokines, MSC-educated- and control macrophages were stimulated with either 1 µg/mL LPS for 24 hours (for IL-10 analysis); 1 µg/mL LPS for 5 hours (for IL-6 analysis); 2000 IU/mL IFN-γ for 2 hours followed by 1 µg/ml LPS for 24 hours (for IL-12 analysis); or 1 µg/ml Ionomycin with 50 nM PMA for 5 hours (for TNF-α analysis). Brefeldin A (Invitrogen) or Monensin (eBioscience) was added to block cytokine secretion, and the cells were stained using Fix & Perm kit (Invitrogen). Briefly, after blocking of Fc receptor-mediated non-specific binding, cells were stained with CD90-PerCP-Cy5.5 and CD14-APC for 15 minutes at room temperature. Cells were then fixed, washed, and permeabilized. Cytokine-specific antibodies, listed in Table 2, were added to the cells followed by 20-minute incubation at room temperature.

TABLE 2

Antibodies used for intracellular cytokine expression analysis.

| Antibody | Label | Source |
| --- | --- | --- |
| anti-IL10 | Phycoerythrin | RnD systems |
| anti-IL12 | Phycoerythrin | Miltenyi Biotech |
| anti-IL6 P | Phycoerythrin | RnD systems |
| anti-IL10 | Phycoerythrin | Miltenyi Biotech |
| anti-IL10 | unconjugated | RnD systems |

The cells were washed and fixed with 1% PFA in PBS for flow cytometry, as described in Example 2.

Because macrophages cultured in the presence of MSCs expressed the anti-inflammatory macrophage marker CD206, the cells were analyzed for intracellular cytokine expression to further characterize their immunophenotype. Intracellular, rather than secreted, cytokines were analyzed because this method directly defined the cytokine expression profile of the macrophages and their various subtypes, e.g., $CD206^+$ compared to $CD206^-$ macrophages. Also, intracellular staining unequivocally identified macrophages, rather than MSCs, as the source of the cytokine under investigation.

Figure 2A:
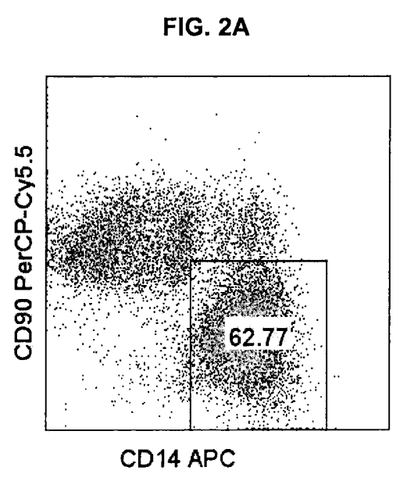
FIG. 2A-D illustrate intracellular expression of IL-10 in MSC co-cultured- and control macrophages.
Figure 2B:
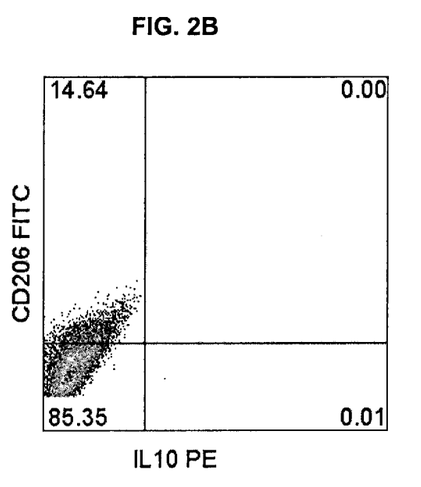
Figure 2C:
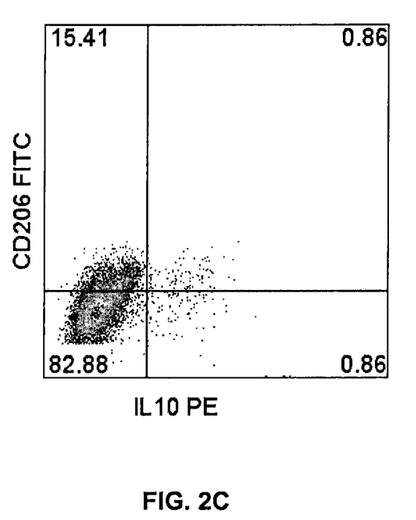
Figure 2D:
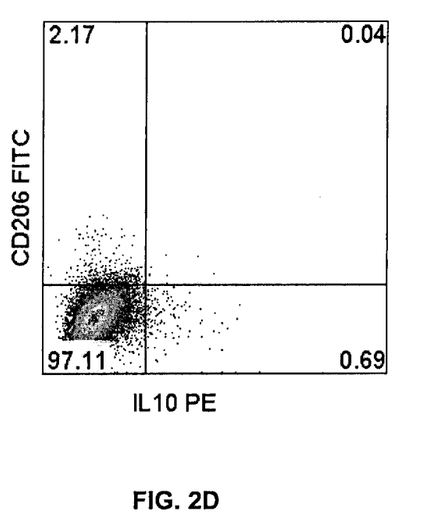
Figure 3A:
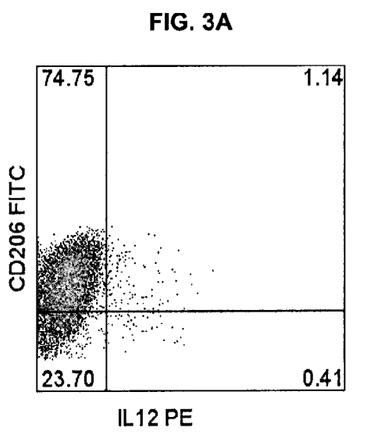
FIG. 3A-F illustrate intracellular cytokine expression of IL-12, IL-6, and TNF-α in MSC co-cultured- and control macrophages.
Figure 3B:
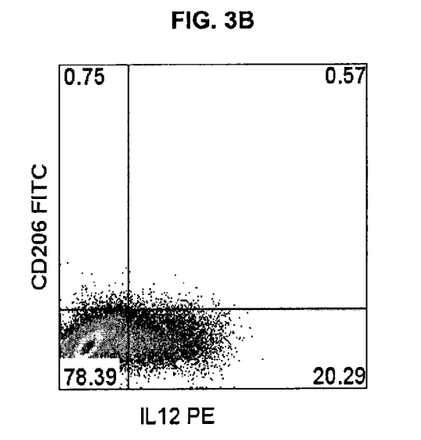
Figure 3C:
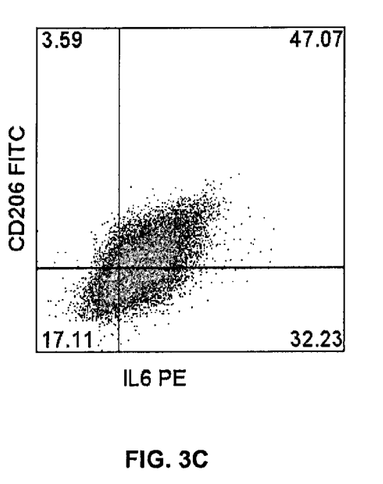
Figure 3D:
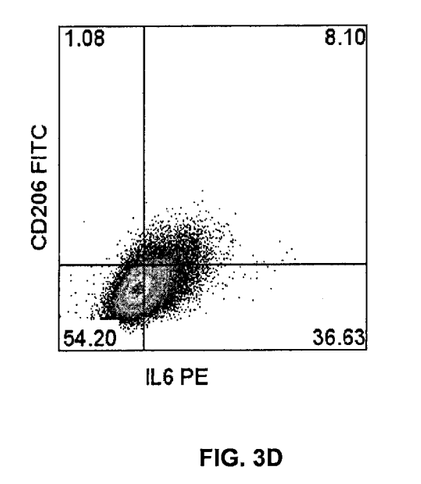
Figure 3E:
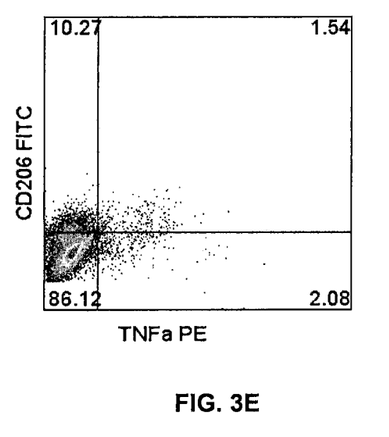
Figure 3F:
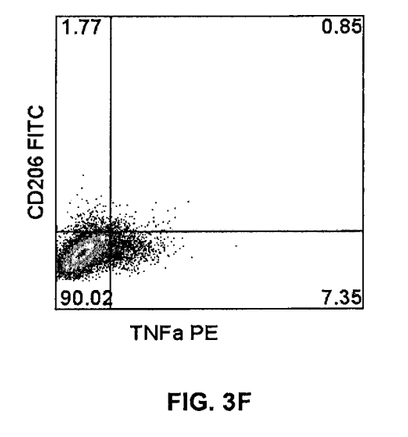

Macrophages co-cultured with MSCs expressed significantly higher levels of intracellular IL-10 (FIG. 2C) and IL-6 (FIG. 3C), compared to control macrophages (FIG. 2D and FIG. 3D, respectively). In contrast, MSC-co-cultured macrophages express significantly lower levels of IL-12 (FIG. 3A) and TNF-α (FIG. 3E), compared to control macrophages (FIG. 3B and FIG. 3F, respectively). Expression of IL-10 was 3.02±2.00 and of IL-6 was 1.74±0.76-fold increased, while IL-12 and TNF-α expressions were 0.34±0.19 and 0.38±0.17-fold decreased in MSC-co-cultured macrophages, compared to controls.

Figure 5:
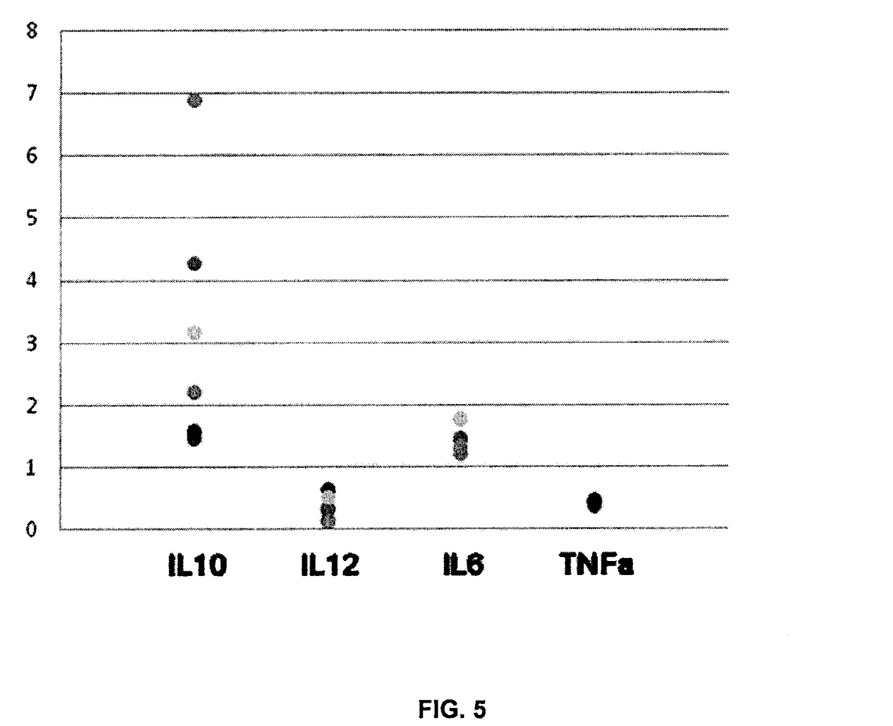
FIG. 5 illustrates the effect of MSC co-culture on macrophage cytokine expression compared to control macrophages.

The ratios were calculated for each cytokine by dividing the percentage of MSC co-cultured macrophages positive for intracellular expression of a particular cytokine by the percent of control macrophages positive for that cytokine (FIG. 5). These ratios reveal that MSC-educated macrophages are IL-10 high, IL-12 low, IL-6 high and TNF-α low (FIG. 5) and constitute a new type of alternatively-activated macrophages different from any known macrophage subtypes.

Example 4

MSC-Induced Macrophage Phagocytic Activity

MSCs were harvested from healthy BM and passaged as described in Example 1. Macrophages were derived as described in Example 1. MSCs-macrophage co-culture experiments were conducted as described in Example 2. Subsequently, macrophages were examined for intracellular cytokine expression and phagocytosis.

To determine if MSCs affect the macrophage phagocytic activity, macrophages were incubated with Alexa 488-conjugated *E. coli* (Invitrogen) for 1 hour at 37° C. To control for non-specific attachment of *E. coli* cells to macrophages, separate control cells were incubated with Alexa 488-conjugated *E. coli* (Invitrogen) for 1 hour at 4° C. Cells were washed with cold PBS twice and harvested using a cell scraper. To block non-specific antibody binding, cells were treated with Fc Receptor blocker for 10 minutes and subsequently stained with CD90-PerCP-Cy5.5 and CD14-APC for 30 minutes at 4° C. After washing, cells were fixed with 1% PFA in PBS and stored for less than 24 hours until analysis.

Figure 4A:
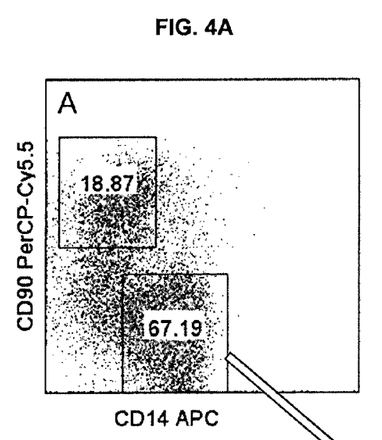
FIG. 4A-D illustrate phagocytosis in MSC co-cultured- and control macrophages.
Figure 4B:
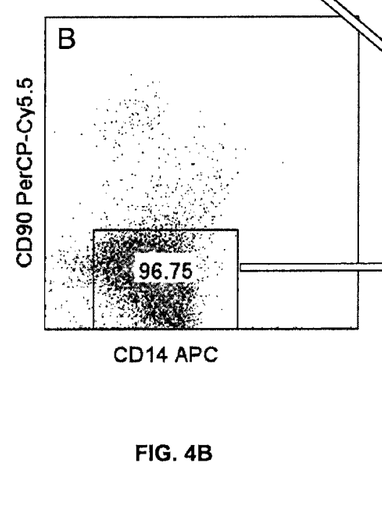
Figure 4C:
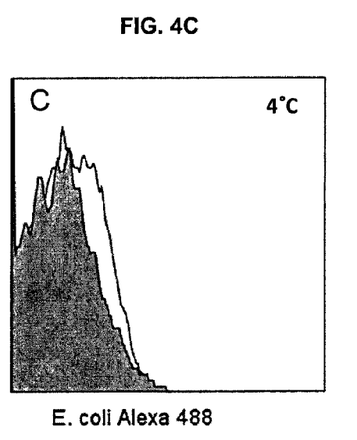
Figure 4D:
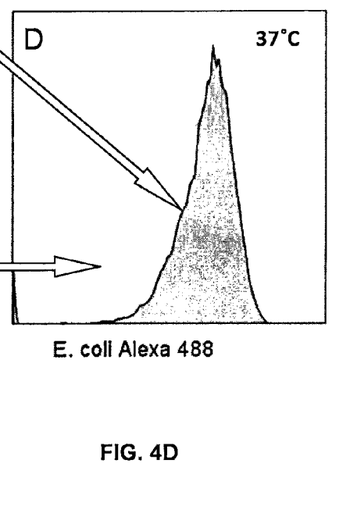

Macrophages co-cultured with MSCs and control macrophages were gated using CD14 and CD90 (FIGS. 4A and 4B, respectively). Nonspecific attachment of *E. coli* to macrophages co-cultured with MSCs or control macrophages was negligible, as demonstrated by incubation at a temperature (4° C.) that does not permit phagocytosis (FIG. 4C). Macrophages co-cultured with MSCs at 37° C. were significantly more phagocytic (FIG. 4D, gray shading), compared to control macrophages (FIG. 4D, no shading). As nonspecific surface attachments of *E. coli* were comparable in MSC co-cultured macrophage and control macrophages (FIG. 4C), the observed 5.80+−1.81-fold increase in phagocytosis of MSC co-cultured macrophages at 37° C. was due to phagocytosis, not to nonspecific attachment (p value=0.044).

Example 5

Wound Healing (Prophetic)

MSCs are harvested from healthy BM and passaged as described in Example 1. Macrophages are derived as described in Example 1. MSCs-macrophage co-culture experiments are conducted as described in Example 2. Subsequently, a therapeutically effective number of MSC-educated macrophages are administered, either by local or systemic injection or by topical application, to individuals afflicted with chronic wounds. Control groups 1 and 2 receive unmodified macrophages and saline solution, respectively. After a period of time, improved wound healing is observed in individuals that receive MSC-educated macrophages, when compared to control individuals.

We claim:

1. An ex vivo generated population of human anti-inflammatory macrophages that is IL-6 high, IL-10 high, IL-12 low, and TNF-α low.

2. The population of human anti-inflammatory macrophages of claim 1, wherein the macrophages express CD 206.

3. A composition comprising:
   human MSC-educated macrophages effective to alleviate a condition associated with inflammation; and
   a pharmaceutically acceptable carrier.

4. The composition of claim 3, wherein the carrier is selected from the group consisting of liquid, oil, lotion, salve, cream, foam, gel, paste, powder, film, and hydrogel.

5. The composition of claim 3, wherein the human MSC-educated macrophages are characterized by a IL-6 high, IL-10 high, IL-12 low, and TNF-α low immunophenotype.

6. The composition of claim 3, wherein the condition is a non-healing wound.

7. The composition of claim 3, wherein the condition is diabetes.

8. The population of human anti-inflammatory macrophages of claim 1, wherein the macrophages are obtained from peripheral blood.

9. The composition of claim 3, wherein the human MSC-educated macrophages are derived from human peripheral blood macrophages.

* * * * *